United States Patent [19]

Wright

[11] 4,228,103
[45] Oct. 14, 1980

[54] EFFECTING CONDENSATION OF NITROHALOARENE AND FORMYL DERIVATIVE OF A PRIMARY AROMATIC AMINE WITH ALKALI METAL HYDROXIDE

[75] Inventor: Robert L. Wright, Fairlawn, Ohio

[73] Assignee: Monsanto Company, St. Louis, Mo.

[21] Appl. No.: 885,968

[22] Filed: Mar. 13, 1978

[51] Int. Cl.$^2$ .................... C07C 85/12; C07C 89/00
[52] U.S. Cl. ...................... 260/576; 260/571
[58] Field of Search ................. 260/571, 576

[56] References Cited

U.S. PATENT DOCUMENTS

| | | | |
|---|---|---|---|
| 1,882,759 | 10/1932 | Britton et al. | 260/576 |
| 2,442,952 | 6/1948 | Kitchens | 260/562 R |
| 2,924,620 | 2/1960 | Miller | 260/576 |
| 3,055,940 | 9/1962 | Merz | 260/576 |
| 3,099,689 | 7/1963 | Cragg | 260/562 R |
| 3,393,241 | 7/1968 | Nielsen | 260/576 |

FOREIGN PATENT DOCUMENTS

| | | | |
|---|---|---|---|
| 498077 | 12/1953 | Canada | 260/576 |
| 1056619 | 5/1959 | Fed. Rep. of Germany | 260/576 |
| 1455207 | 11/1976 | United Kingdom | 260/576 |

OTHER PUBLICATIONS

Sharnin, et al., "J. Org. Chem., USSR", vol. 6, pp. 990–992 (1970).

Rondestvedt, "J. Org. Chem.", vol. 42 (10), pp. 1786–1790 (1977).

*Primary Examiner*—John Doll
*Attorney, Agent, or Firm*—Gordon B. Seward

[57] ABSTRACT

Preparation of nitrodiarylamine by reacting alkali metal hydroxide, activated aromatic amine and nitrohaloarene is described.

11 Claims, No Drawings

EFFECTING CONDENSATION OF NITROHALOARENE AND FORMYL DERIVATIVE OF A PRIMARY AROMATIC AMINE WITH ALKALI METAL HYDROXIDE

The invention relates to the preparation of nitrodiarylamines which are valuable intermediates for the preparation of dyestuffs and antidegradants. For example, 4-nitrodiphenylamine is an important intermediate for rubber antidegradants. The invention particularly relates to the preparation of 4-nitrodiphenylamine from p-nitrochlorobenzene.

Nitrodiarylamines form by condensing a nitrohaloarene with the formyl derivative of a primary aromatic amine in the presence of a so-called acid acceptor for which purpose powdered potassium carbonate is commonly used. Although sodium formanilide is known to condense with p-nitrochlorobenzene in dimethyl formamide to form p-nitrodiphenylamine, such solvent is rather expensive for commercial use. Moreover, an additional step is required to form the salt.

It has now been discovered that nitrodiarylamine is formed in a single step by gradually mixing aqueous alkali metal hydroxide with the formyl derivative of a primary aromatic amine and nitrohaloarene at condensation temperature for forming nitrodiarylamine and concurrently removing water from the reaction zone during the mixing and condensation. Preferably, the aqueous alkali metal hydroxide is gradually added to a reactor at condensation temperature and the other reactants; namely, formyl derivative and nitrohaloarene, independently are either already present in the reactor at condensation temperature or added concurrently with the aqueous alkali metal hydroxide. The addition may be continuous, but should be at a rate slow enough to avoid substantial build-up of water. It is believed that the process succeeds because the procedure minimizes hydrolytic side reactions. Thus, it appears that the optimum operating conditions are realized when the water is removed at 170°–185° C. at substantially the rate it appears in the reactor. The water which appears in the reactor comprises that added with the alkali metal hydroxide and that formed in the condensation.

The preferred alkali metal hydroxide is potassium hydroxide. Cesium and rubidium hydroxides are comparable but more expensive. Sodium hydroxide is less efficacious but the efficiency is improved by using sodium hydroxide with a potassium, cesium or rubidium compound. Condensation temperature is usually within the range of 140°–215° C. depending upon the reactants. Preferably, the condensation is carried out at 170°–205° C.

A variety of nitrohaloarenes have been proposed for making nitrodiarylamines, any of which appear to be suitable for use in the process of the invention. Illustrative of nitrohaloarenes believed to be suitable in the process are: o-nitrochlorobenzene, o-nitrobromobenzene, p-nitrochlorobenzene, p-nitrobromobenzene, m-nitrochlorobenzene, m-nitrobromobenzene, 1-chloro-2-methyl-4-nitrobenzene, 1-chloro-3-methyl-4-nitrobenzene, 1-chloro-2-nitronaphthalene, 3,4-dichloronitrobenzene, 3-methyl-4-chloronitrobenzene, 2-methyl-4-chloronitrobenzene, 2-ethyl-4-chloronitrobenzene, 2,3-dimethyl-4-chloronitrobenzene, 2,4-dimethyl-4-chloronitrobenzene, 3,5-dimethyl-4-chloronitrobenzene and p-nitrofluorobenzene.

The process is believed to be a general one for condensation of the formyl derivative of an aromatic primary amine. Suitable examples are formanilide and formanilide substituted in the benzene nucleus by one or more substituents inert under the reaction conditions; for example, one or more alkyl, alkoxy, fluoro, chloro or nitro substituents. Illustrative substituted formanilides which may be used in the process are: m-chloroformanilide, p-chloroformanilide, 2-methylformanilide, 3-methylformanilide, 4-methylformanilide, 3-ethylformanilide, 3,4-dimethylformanilide, 3-methoxyformanilide, 4-methoxyformanilide, 4-ethylformanilide, 4-isopropylformanilide, 4-butylformanilide, 3,4-dichloroformanilide and 4-nitroformanilide.

It is presumed that the process involves the transient formation of alkali metal formanilide which is the immediate precursor of the nitrodiarylamine. Reaction temperature, amount of alkali metal hydroxide and the rate of mixing are significant. With KOH, the reaction temperature is preferably within the range of 170°–205° C., and the KOH within the range of 1.2–1.8 moles per mole of nitrohaloarene. The general preferred temperature of reaction is believed to be that at which the rate of condensation with nitrohaloarene is sufficiently more rapid than the rate of hydrolysis of alkali metal formanilide, so that the hydrolysis does not predominate; but, the invention is not limited to any theory of the reaction mechanism and does not depend on the correct explanation for the observation and discoveries made.

DESCRIPTION OF PREFERRED EMBODIMENTS

Example 1

Into a suitable reactor fitted with a condenser and water trap are charged 49.7 grams (0.315 moles) of p-nitrochlorobenzene, together with 98.7 grams of a 66.4% solution of formanilide in xylene recovered from a previous run (0.54 molecular proportions). The solution also contains 0.07 moles of para-nitrochlorobenzene, bringing the total to 0.385 moles. About 50 milliliters of xylene are added; and the mixture heated to refluxing temperatures which is about 195°–198° C. To the hot mixture is added, at the rate of about 0.3 milliliters per minute, 45% aqueous potassium hydroxide. A total of 0.55 mole is added over a period of about 175 minutes at a temperature of about 195° C., during which time the water is continuously removed. The heating is continued for about 10 minutes after addition of the aqueous potassium hydroxide to be sure that all the water is removed. The reaction mixture is diluted with xylene, washed with water and the washed xylene solution cooled to induce crystallization of the 4-nitrodiphenylamine, which is separated by filtration. The amounts in the mother liquor of 4-nitrodiphenylamine product and unreacted p-nitrochlorobenzene are determined by gas-liquid chromatography. The yield of 4-nitrodiphenylamine totals about 80% and the conversion of p-nitrochlorobenzene charged is about 90%. The results are comparable when 0.7 mole of 45% KOH is added at 169°–180° C. over a period of about 230 minutes.

The operational advantages of the foregoing examples as compared to the reaction with powdered $K_2CO_3$ are elimination of solids handling, elimination of particle size as a variable, and reduction of by-product gas evolution because evolution of carbon dioxide is eliminated. In a variation of the foregoing example, the formanilide and 45% KOH (0.70 moles) are fed concurrently to the p-nitrochlorobenzene and xylene at 170° C. over a period of about 225 minutes. The yield of 4-nitrodiphenylamine is 79%, and the conversion about 88%. The results indicate that the reaction may be carried out continuously if desired.

Using sodium hydroxide, the process is operative, at least over the range of 140°–190° C.; but a reaction temperature of about 180° C. is preferred. The sodium hydroxide charge is desirably about 1.8 mole per mole of p-nitrochlorobenzene and is preferably used in conjunction with a compound of potassium, cesium or rubidium, for example, KCl, as a reaction promoter. A charge of 0.25 mole of KCl per mole of p-nitrochlorobenzene is sufficient.

Examples 2 and 3

Although the condensation temperature is less than optimum in these examples, they illustrate the influence of KCl. A reactor fitted with a condenser, water trap and means for feeding aqueous solution is charged with 65.4 grams (0.54 mole) of formanilide and 60.6 grams (0.385 mole) of p-nitrochlorobenzene. In one case, 14.8 grams (0.2 mole of KCl is also charged to the reactor. The contents of the reactor are heated to 160°–166° C. and 50% aqueous sodium hydroxide gradually fed over a period of 2.5-3 hours while water is continuously separated. The 4-nitrodiphenylamine is determined as described in Example 1. The reaction times, moles of NaOH, moles of KCl, liters of CO, % yield of 4-nitrodiphenylamine and % conversion of p-nitrohalobenzene are as follows:

| Example No. | Time Hrs. | NaOH Moles | KCl Moles | CO evolved liters | Yield % | Conversion % |
|---|---|---|---|---|---|---|
| 2 | 2.5 | .7 | none | .7 | 42.9 | 46.4 |
| 3 | 3.0 | .6 | .2 | 1.9 | 52.2 | 62.4 |

It will be noted from the foregoing that yield and conversions are both increased by having KCl in the reactor. The improvements are even greater at 180°–185° C. It is also preferred to add the KCl with the NaOH. Example 4 illustrates a preferred embodiment using sodium hydroxide.

Example 4

Into a suitable reactor fitted with a condenser and water trap are charged 65.4 parts by weight (0.54 mole) of formanilide and 60.6 parts by weight (0.385 mole) of p-nitrochlorobenzene. The mixture is heated to 180°–185° C. and an aqueous solution containing 0.6 mole of NaOH and 0.1 mole of KCl is added over a period of about 3.25 hours during which time the water is continuously separated. The 4-nitrodiphenylamine is determined as described in Example 1 to obtain a 71% yield, the conversion being 77%. Reducing the NaOH to 0.4 moles and adding the NaOH, KCl in 2¾ hours at 180°–185° C. reduces the yield to 46.2% and conversion to 47.3%. On the other hand, conversion is essentially 100% and yield about 85% when the NaOH is increased to 0.7 mole and the NaOH-KCl added over about 5 hours in accordance with other preferred embodiments illustrated in Examples 5-8.

Examples 5-8

An aqueous solution of NaOH and KCl is added to a mixture of 0.54 mole of formanilide and 0.385 mole of p-nitrochlorobenzene at 180°–185° C. as described in Example 4. In these runs the aqueous solution is fed through one arm of a Y tube and a slight nitrogen pressure applied to the other. The nitrogen purge prevents plugging of the feed tube due to deposition of solids. The 4-nitrodiphenylamine is determined as described in Example 1 to obtain results as follows:

| Example | Time of addition of aqueous solution - hrs. | NaOH Moles | KCl Moles | Yield % | Conversion % |
|---|---|---|---|---|---|
| 5 | 5 | 0.40 | 0.3 | 57.4 | 62.6 |
| 6 | 5 | 0.77 | 0.1 | 85.7 | 100. |
| 7 | 5.75 | 0.74 | 0.1 | 84.9 | 100. |
| 8 | 5 | 0.70 | 0.1 | 85.2 | 99. |

The molar ratio of the promoter advantageously used with sodium hydroxide is usually 0.025-1.0 mole equivalent and preferably 0.5-0.7 mole equivalent of metal per mole of nitrohaloarene. In compounds of potassium, cesium and rubidium effective for promoting the reaction, the anion appears to be largely a matter of choice, examples being halogen, carbonate, bicarbonate, sulfate or acyl such as formate, acetate and benzoate or the anion from the formyl derivative of an aromatic amine. It should be borne in mind, however, that strong alkalis like KOH foster side reactions and should be used in accordance with the principles of this invention. Although the promoting effect of the metal may in some instances be obscured by adverse effects of the anion, a simple experiment or two will show whether a given potassium, cesium or rubidium compound is effective in promoting the reaction. Representative examples of promoters are potassium formanilide, cesium chloride, rubidium carbonate, potassium acetate, potassium benzoate, potassium sulfate and potassium bromide.

Example 9

Into the reactor previously described are charged 49.7 grams (0.315 moles) of p-nitrochlorobenzene together with 98.7 grams of a 66.4% solution of formanilide recovered from a previous run (0.54 molecular proportions). The solution also contained 0.07 moles of p-nitrochlorobenzene, bringing the total to 0.385 mole. About 50 milliliters of xylene are added, and the mixture heated to refluxing temperature which is about 195°–198° C. To the hot mixture is added at the rate of about 0.4 ml. per minute 82.5 grams (0.55 mole) of cesium hydroxide as a 50% solution in water (165 grams) during which addition the water is continuously removed. The heating is continued for a total time of about five hours, then 250 ml. of xylene is added and the xylene solution washed twice with 200 ml. portions of 90° C. water. The xylene solution is cooled to 5° C., filtered and the cake washed with 60 ml. of 5° C. xylene. There is obtained 40.7 grams of 4-nitrodiphenylamine. The total yield determined as described in Example 1 is 72%. The conversion of p-nitrodiphenylamine is 99.1%.

Example 10

Rubidium hydroxide is substituted for cesium hydroxide in Example 9, employing 66.2 grams (0.55 moles) of RbOH.H$_2$O to which is added 44.1 grams of water to provide a 60% solution. The solution is added at a rate of 0.4 ml. per minute while heating at 193°–198° C. The total heating time is 187 minutes, after which 49 grams of 4-nitrodiphenylamine is isolated as described in Example 3. The total yield determined as described in Example 1 is 78% and conversion of p-nitrochlorobenzene is 100%.

Example 11

To a charge of 157 grams of p-nitrochlorobenzene (1 mole), 169 grams of formanilide (1.4 moles) and 50 grams of xylene at 180° C. is fed over a period of about 4 hours a solution of 58 grams of potassium carbonate (0.42 mole) and 22.5 grams of sodium hydroxide (0.56 mole) in 120 grams of water. Water is removed concurrently from the reaction mixture with the addition of the aforesaid solution. The temperature of the reaction mixture is then raised to 205° C. and heated at such temperature for 1½ hours. The amounts of 4-nitrodiphenylamine formed and p-nitrochlorobenzene remaining unreacted are then determined, as described in Example 1. The yield of 4-nitrodiphenylamine is 69.3%, and the conversion of the p-nitrochlorobenzene charged is 78.4 or 88.4%.

Example 12

In an experiment without potassium, the reactor charge is 85 grams of formanilide (0.7 mole), 78.5 grams of p-nitrochlorobenzene and 50 grams of xylene. The aqueous reactant is 28 grams of sodium hydroxide (0.7 mole) in 50 ml. of water. The reactor charge is heated to 210° and the aqueous reactant added over a period of 3 hours. The reactor contents are then heated to 215° C. for 1 hour and the yield of 4-nitrodiphenylamine and unreacted p-nitrochlorobenzene determined as described in Example 1. The yield is 68.6% and conversion 84.9%. It will be noted that the yield is slightly lower in the control experiment and by-products increased as evidenced by the higher conversion; and, therefore, the reaction efficiency which the percent of p-nitrochlorobenzene consumed that is converted to 4-nitrodiphenylamine is improved.

Although the invention has been illustrated by typical example, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. The process which comprises forming nitrodiarylamine by gradually mixing aqueous alkali metal hydroxide with the formyl derivative of an aromatic primary amine and reactive nitrohaloarene at condensation temperature for forming nitrodiarylamine and concurrently removing water, wherein the aqueous alkali metal hydroxide is added at a rate slow enough to avoid substantial buildup of water.

2. The process which comprises forming nitrodiarylamine by gradually mixing at condensation temperature for forming nitrodiarylamine
   (A) formanilide or formanilide substituted in the benzene nucleus with one or more alkyl, alkoxy, fluoro, nitro, or chloro substituents,
   (B) nitrohalobenzene and
   (C) aqueous alkali metal hydroxide and concurrently removing water,
wherein (C) is gradually added to a reactor at condensation temperature, (A) and (B) independently either being present in the reactor or added concurrently with (C), and (C) is added at a rate slow enough to avoid substantial buildup of water.

3. The process of claim 2 wherein (C) is potassium hydroxide.

4. The process of claim 2 wherein A is formanilide and B is p-nitrochlorobenzene.

5. The process of claim 2 wherein the condensation temperature is 180°–200° C., (A) is formanilide, (B) is p-nitrochlorobenzene and (C) is aqueous sodium hydroxide.

6. The process of claim 2 wherein (A) is formanilide, (B) is p-nitrochlorobenzene and (C) is aqueous sodium hydroxide and a potassium compound in reaction promoting amount.

7. The process of claim 6 wherein the potassium compound is potassium chloride.

8. The process of claim 6 wherein the potassium compound is potassium carbonate.

9. The process of claim 6 wherein the potassium compound is potassium acetate.

10. The process of claim 2 wherein (C) is rubidium hydroxide.

11. The process of claim 2 wherein (C) is cesium hydroxide.

* * * * *